(12) United States Patent
Wieters

(10) Patent No.: US 10,085,621 B2
(45) Date of Patent: Oct. 2, 2018

(54) ENDOSCOPE HAVING A SIDEWAYS VIEWING DIRECTION

(71) Applicant: OLYMPUS WINTER & IBE GMBH, Hamburg (DE)

(72) Inventor: Martin Wieters, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 411 days.

(21) Appl. No.: 14/150,989

(22) Filed: Jan. 9, 2014

(65) Prior Publication Data

US 2014/0128679 A1 May 8, 2014

Related U.S. Application Data

(63) Continuation of application No. PCT/EP2012/002791, filed on Jul. 3, 2012.

(30) Foreign Application Priority Data

Jul. 11, 2011 (DE) .................. 10 2011 078 968

(51) Int. Cl.
*A61B 1/00* (2006.01)
*A61B 1/05* (2006.01)

(52) U.S. Cl.
CPC ...... *A61B 1/00177* (2013.01); *A61B 1/00096* (2013.01); *A61B 1/00179* (2013.01); *A61B 1/05* (2013.01); *A61B 1/051* (2013.01)

(58) Field of Classification Search
USPC ........................................................ 600/173
See application file for complete search history.

(56) References Cited

U.S. PATENT DOCUMENTS 4,571,023 A 2/1986 Ono
5,253,638 A 10/1993 Tamburrino et al.
(Continued)

FOREIGN PATENT DOCUMENTS

EP 1 787 570 A1 5/2007
JP S59-211429 A 11/1984
(Continued)

OTHER PUBLICATIONS

Japanese Office Action dated May 4, 2015 from related Japanese Patent Application No. 201280033699.0, together with an English language translation.
(Continued)

*Primary Examiner* — Alexandra L Newton
(74) *Attorney, Agent, or Firm* — Scully, Scott, Murphy & Pressr, P.C.

(57) ABSTRACT

A sideways viewing endoscope including: a proximal handle, an endoscope shaft having outer and inner tubes, and first and second optical component assemblies arranged in a distal region of the endoscope shaft, the optical components assemblies can be rotated with respect to one another about a longitudinal axis of the endoscope shaft and are mounted against each other by an axial bearing that is disposed between the optical component assemblies and pretensioned by a pretensioning device; wherein the first optical component assembly is distally connected to the outer tube and comprises optical windows, prisms and/or lenses having a sideways viewing direction and the second optical component assembly is distally connected to the inner tube and comprises an image sensor having a straight-ahead viewing direction oriented in the direction of the longitudinal axis; and the pretensioning device is disposed in the distal region of the endoscope shaft at the axial bearing.

6 Claims, 2 Drawing Sheets

(56) References Cited

U.S. PATENT DOCUMENTS

| | | | | |
|---|---|---|---|---|
| 5,512,036 | A | * | 4/1996 | Tamburrino ....... A61B 1/00096 433/29 |
| 5,609,561 | A | | 3/1997 | Uehara et al. |
| 5,621,830 | A | * | 4/1997 | Lucey ................ A61B 1/00179 385/118 |
| 5,961,445 | A | * | 10/1999 | Chikama ............ A61B 1/00096 600/112 |
| 6,537,209 | B1 | | 3/2003 | Pinkhasik et al. |
| 6,616,602 | B1 | * | 9/2003 | Witte ................. G02B 23/2476 600/163 |
| 7,713,189 | B2 | * | 5/2010 | Hanke ................ A61B 1/00183 600/109 |
| 2006/0058581 | A1 | * | 3/2006 | Hanke ................ A61B 1/00183 600/109 |
| 2009/0326327 | A1 | | 12/2009 | Hirata et al. |
| 2014/0128674 | A1 | | 5/2014 | Wieters |

FOREIGN PATENT DOCUMENTS

| | | |
|---|---|---|
| JP | 2010-008493 A | 1/2010 |
| JP | 2014-523323 A | 9/2014 |

OTHER PUBLICATIONS

International Search Report dated Oct. 5, 2012 issued in PCT/EP2012/002791.
Chinese Office Action dated May 4, 2015 from related Chinese Patent Application No. 201280033699.0, together with an English language translation.

* cited by examiner

ENDOSCOPE HAVING A SIDEWAYS VIEWING DIRECTION

CROSS-REFERENCE TO RELATED APPLICATION

The present application is a continuation of PCT/EP2012/002791 filed on Jul. 3, 2012, which is based upon and claims the benefit to DE 10 2011 078 968.5 filed on Jul. 11, 2011, the entire contents of each of which are incorporated herein by reference.

BACKGROUND

Field

The invention relates to an endoscope having a sideways viewing direction, comprising a proximal handle, an endoscope shaft having an outer tube and an inner tube, and two optical component assemblies which are arranged in the distal region of the endoscope shaft, can be rotated with respect to one another about the longitudinal axis of the endoscope shaft, and are mounted against each other by means of an axial bearing that is disposed between the optical component assemblies and is pretensioned by means of a pretensioning device, wherein a first optical component assembly that is distally connected to the outer tube comprises optical windows, prisms and/or lenses having a sideways viewing direction, and a second optical component assembly that is distally connected to the inner tube comprises an image sensor having a straight-ahead viewing direction and being oriented in the direction of the longitudinal axis of the endoscope shaft.

In the scope of the present invention, the term endoscope refers in particular to video endoscopes, thus endoscopes in connection with at least one image sensor, which is designed to capture a video recording independently of whether the image sensor is disposed distally in the endoscope shaft, proximally in a handle, or externally in a camera head, which can be attached to an ocular in the proximal region of the endoscope, thus on the side of an operator or surgeon.

The term viewing direction also called "direction of view" (DOV), relates to the lateral view or reverse view deviating from the longitudinal axis of the endoscope which is represented as a polar angle, wherein a viewing angle of 0° means a straight-ahead view in the longitudinal direction of the endoscope shaft, while 90°, for example, designates a viewing direction which deviates at a right angle from the straight-ahead view.

Prior Art

With endoscopes, or respectively video endoscopes having a viewing direction of ≠0°, it is necessary to be able to rotate two optical component assemblies in the distal optical system with respect to each other. A radial and an axial bearing of the optical component assemblies are necessary for this purpose. The radial bearing limits the relative movement of the component assemblies with respect to each other in radial direction, the axial bearing limits the relative movement in the axial direction of the endoscope. In order to avoid negatively impacting the optical quality, it is further advantageous if the axial bearing is designed to be free of play, so that there is no change in the optical path due to an axial movement of the optical component assemblies with respect to each other.

In the prior art, freedom from axial play is created by pretensioning the bearing with a spring, for example a spiral spring located in the handle region of the endoscope.

With the video endoscope according to the document EP 1 787 570 B1, there is a radially acting bearing located in the handle. There is both a radial and an axial bearing located between the two distal optical component assemblies. An axial force is exerted on this bearing by means of a spring in the handle. Both the torque and the axial force are transferred using two tubes, to each of which an optical component assembly is attached. This way, the distally disposed axial bearing is held free of axial play due to the spring placed in the handle region.

Using the spring placed in the handle for pretensioning the axial bearing with endoscopes of the prior art, axial forces must be transferred in addition to the torque. Because of this, the construction is relatively complicated and involved.

Based on this prior art, the object of the present invention is to provide an endoscope that has a sideways viewing direction and two optical component assemblies in the distal region of the endoscope shaft that can rotate relative to each other, and with which optimal optical quality is guaranteed at all times.

SUMMARY

This object is achieved by an endoscope, in particular a video endoscope, having a sideways viewing direction, comprising a proximal handle, an endoscope shaft having an outer tube and an inner tube, and two optical component assemblies which are arranged in the distal region of the endoscope shaft, can be rotated with respect to one another about the longitudinal axis of the endoscope shaft, and are mounted against each other by means of an axial bearing that is disposed between the optical component assemblies and is pretensioned by means of a pretensioning device, wherein a first optical component assembly that is distally connected to the outer tube comprises optical windows, prisms and/or lenses having a sideways viewing direction and a second optical component assembly that is distally connected to the inner tube comprises an image sensor having a straight-ahead viewing direction being oriented in the direction of the longitudinal axis of the endoscope shaft, that is further developed in that the pretensioning device is disposed in the distal region of the endoscope shaft at the axial bearing.

Due to the fact that the pretensioning device is disposed in the distal region of the endoscope shaft at the axial bearing, the force impact occurs directly at the axial bearing and need not be transferred via the tubes sliding within one another. This leads to an axial bearing that is very efficient, continuously reliable, and free of play. The axial bearing no longer depends on the axially acting force being transferred via the inner tube, so that there are no frictional losses due to friction of the inner tube and outer tube, and also no longer any grabbing due to friction during rotation of the inner tube with respect to the outer tube. Furthermore, additional tubes for transferring axially acting forces can be omitted so that the placement according to the invention of the pretensioning device also leads to a simple and uncomplicated design.

Due of the fact that the axial bearing is disposed between the optical component assemblies, the axial bearing at all times defines the correct position of the second component assembly with respect to the first component assembly such that a constant optical quality is guaranteed.

According to the invention, the first optical component assembly is understood to be the distally disposed sideways viewing optical component assembly having entry window, diversion elements such as mirrors or prisms for example, and lens elements, if applicable, while the second optical component assembly is the assembly which is responsible for further transmission of light within the endoscope shaft up to an image sensor device. The optical elements of the second optical component assembly are therefore typically disposed pointing in the longitudinal direction of the endoscope shaft, and can be an image sensor and for example lenses or lens groups.

In an advantageous design of the endoscope according to the invention, at least one part of the axial bearing and/or one optical component assembly has a ferromagnetic material and the pretensioning device comprises a magnet, in particular an annular magnet, by means of which the ferromagnetic material is attracted in the direction of a closure of the axial bearing. This means that the magnet is typically disposed on a side opposite the ferromagnetic material with respect to the axial bearing.

In an advantageous variant, the magnet is fastened to the inner tube, wherein the inner tube consists at least to some extent of a paramagnetic or diamagnetic material. In an alternative variant, the magnet is fastened to the outer tube, wherein the outer tube consists at least to some extent of a paramagnetic or diamagnetic material. A magnet can also be provided for both the inner tube and the outer tube, and disposed so that they attract one another.

The formation of the pretensioning device with magnets represents a particularly simple constructive measure.

Alternatively or in addition to this, it is preferably provided that the pretensioning device comprises a tension spring or a thrust spring.

Likewise in an advantageous manner, the pretensioning device comprises alternatively or in addition to this, pretensioned elastic guide elements, in particular a pretensioned elastic guide ring and/or a pretensioned elastic guide bead or guide rib engaging in a guide groove.

In order to prevent also radial play, it is preferably provided that a radial bearing is provided between the inner tube and the outer tube in the distal region of the endoscope shaft and/or the axial bearing is constructed also as a radial bearing. Such a bearing designated also as a "radial axial bearing" is responsible for limiting of the play both in the radial and the axial direction.

The axial bearing is preferably designed as a slide bearing. The axial bearing is also preferably designed as a retainer for optical elements and/or optical component assemblies.

The slide bearing can be built using additional constructive elements composed of ceramic or plastic, and/or can be a direct component of the retainer of the optical component assemblies, e.g., using suitable coatings or surface treatments.

The construction of ferromagnetic material, permanent magnet and axial bearing is preferably selected so that due to the magnetic force an axial force is generated that keeps the axial bearing free of play.

Additionally, the radial bearing disposed between the two optical component assemblies, is, as with the axial bearing, comprised of additional or integral bearing parts.

Further characteristics of the invention will become apparent from the description of the embodiments according to the invention together with the claims and the included drawings. Embodiments according to the invention can fulfill individual characteristics or a combination of several characteristics.

BRIEF DESCRIPTION OF THE DRAWINGS

The invention is described below, without restricting the general intent of the invention, based on exemplary embodiments in reference to the drawings, whereby we expressly refer to the drawings with regard to the disclosure of all details according to the invention that are not explained in greater detail in the text. They show.

In the drawings, the same or similar types of elements and/or parts are provided with the same reference numbers so that a corresponding re-introduction can be omitted.

DETAILED DESCRIPTION

Figure 1:
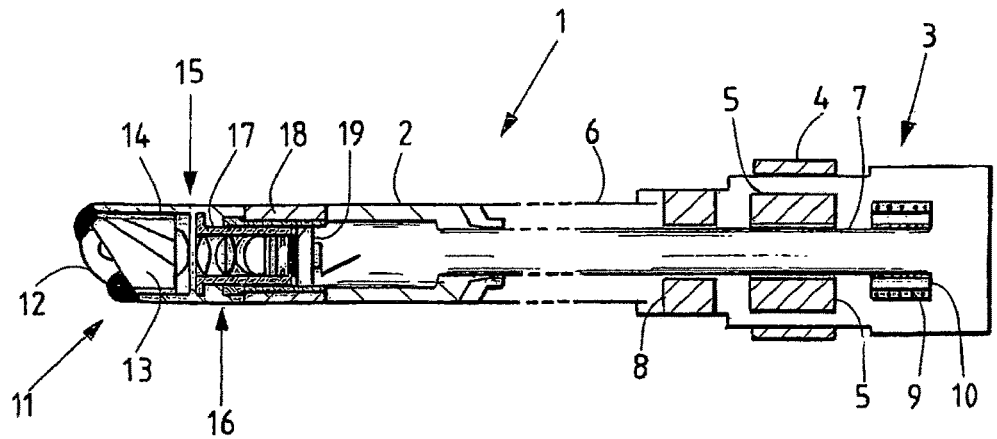
FIG. 1 illustrates a schematic representation of an endoscope according to the prior art.

FIG. 1 schematically represents an endoscope 1 known from the prior art. The endoscope 1 at the proximal end, shown on the right side, has a handle 3 that ends in a shaft 2. The distal end of the shaft 2 is shown on the left side in FIG. 1.

The handle 3 has a rotary ring 4 by means of which, using bar magnets 5 that are connected to an inner tube 7, the inner tube 7 can be rotated with respect to an outer tube 6, in order to change the viewing direction of the endoscope 1. The inner tube 7 is mounted in the handle 3 additionally by means of a radial bearing 8. In addition, the handle 3 comprises a pretensioning device comprised of a compression spring 9, which is pretensioned with respect to a stop 10 for the compression spring 9. The compression spring 9 ensures that the inner tube 7 is pressed, or respectively pretensioned, in the axial direction toward the distal end 11 of the shaft 2.

The shaft 2 at the distal end 11 has a window 12 that views sideways. Behind the window 12, there is an optical component assembly 13 having lenses and prisms with which the light entering through the window 12 is diverted into a direction parallel to the longitudinal axis of the shaft 2. The optical component assembly 13 is held by a retainer 14 which is connected to the outer tube 6. The window 12 is also part of the optical component assembly 13.

A second optical component assembly 16, which in this case ends in an image sensor unit 19, is attached to the first optical component assembly 13. The second optical component assembly 16 is held in a retainer 17, which is connected to the inner tube 7 in such a manner that it also performs the rotations or movements with the inner tube 7. The inner tube 7 in the region of the distal end 11 of the shaft 2, is mounted radially with respect to the outer tube 6 by means of a radial bearing 18.

The distal front surface of the retainer 17 of the second optical component assembly 16 and the proximal front surface of the retainer 14 of the first optical component assembly 13 are disposed opposite from each other and form an axial bearing 15. Due to the pretensioning of the inner tube 7 in the axial direction by the compression spring 9 in the handle 3, the axial bearing 15 is closed, i.e., the distal side front surface of the retainer 17 is pressed against the proximal side front surface of the retainer 14. Thereby, the axial position of the second optical component assembly 16 is definitely defined with respect to the first optical component assembly 13, and optimal optical quality is attained.

Because the axially acting pretensioning force is transferred via the longitudinally extending inner tube 7, each tilting, rotation or movement of the inner tube 7 in the outer tube 6 results in the axially acting pretensioning force not being transferred optimally to the axial bearing 15. This can lead to an impairment of the optical quality.

FIGS. 2 to 5 show example embodiments for the axial bearings according to the invention. Each case shows a detailed section of the distal tip of the shaft 2, which is not shown more explicitly in the following figures. For clarity, in the FIGS. 2 to 5, in each case only the optical component assemblies and the retainers thereof and the axially disposed pretensioning device according to the invention are shown. In principle in these cases, springs or other pretensioning elements in the handle 3 can be completely omitted.

Figure 2:
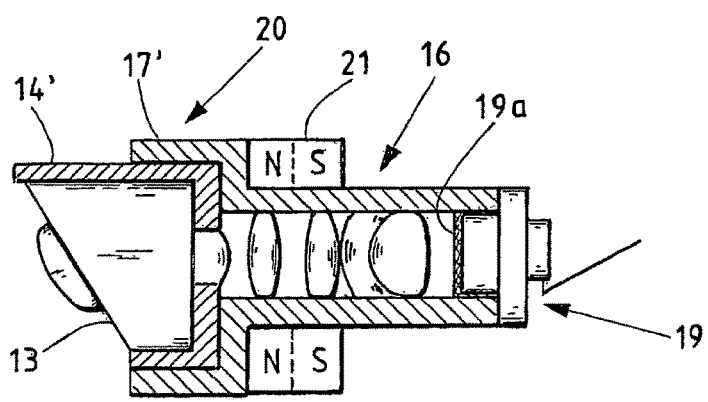
FIG. 2 illustrates a schematic representation of an axial bearing according to the invention.

FIG. 2 schematically shows the first optical component assembly 13 disposed in a retainer 14', which is composed of a ferromagnetic material. The second optical component assembly 16 having a sensor unit 19 and an image sensor 19a, is formed such that it abuts against the proximal front surface of the retainer 17' and also envelops it from the outside. The form-locking construction of retainer 14' and retainer 17' acts as a combined radial bearing and axial bearing. This is attached to an annular magnet 21, which exerts a magnetic force on the ferromagnetic material of the retainer 14' of the first optical component assembly 13, and thus ensures a secure axial support of the retainer 17' on the retainer 14' and vice versa. This embodiment is particularly simple both mechanically and structurally.

Figure 3:
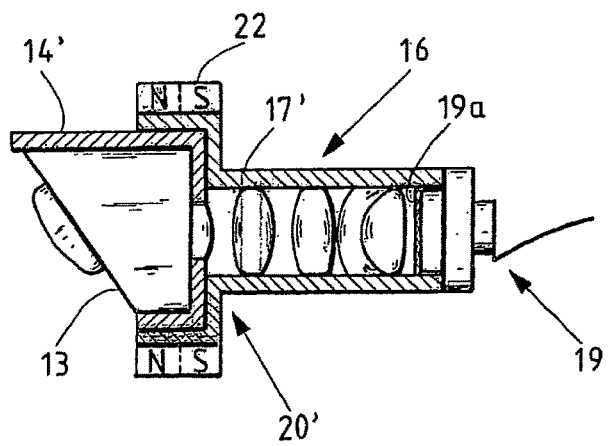
FIG. 3 illustrates a schematic representation of a further axial bearing according to the invention.

FIG. 3 shows an alternative arrangement. In contrast to the arrangement in FIG. 2, in FIG. 3 the annular magnet 22 is not disposed in an imaginary lengthening of the side walls of the retainer 14', but rather in the axial direction of the shaft 2 at the position of the retainer 14'.

Figure 4:
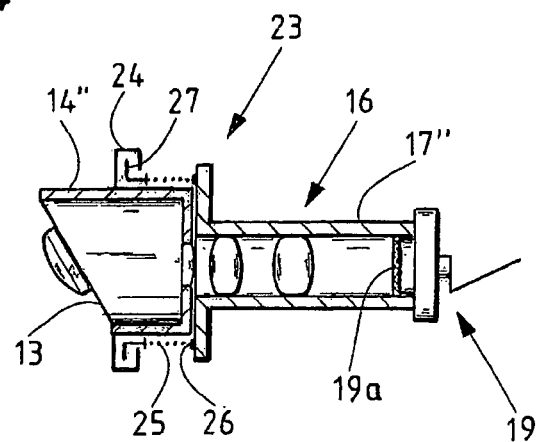
FIG. 4 illustrates a schematic representation of a further axial bearing according to the invention.
Figure 5:
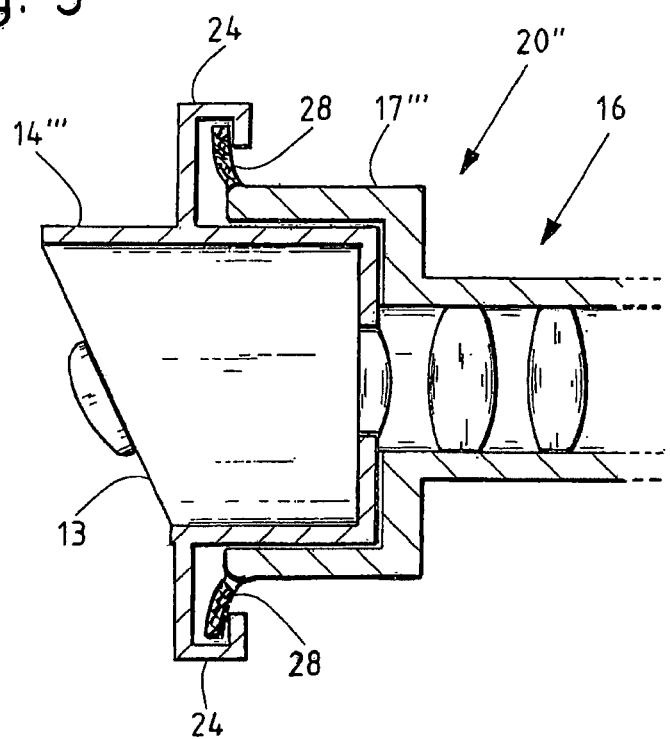
FIG. 5 illustrates a schematic representation of a further axial bearing according to the invention.

FIG. 4 shows an alternative embodiment of a pretensioning device in the distal region of the shaft 2. In this case, the pretensioning device is implemented as a tension spring 25 between the retainer 14" of the first optical component assembly 13 and the retainer 17" of the second optical component assembly 16. The tension spring is fastened to the side of the retaining apparatus 17" of the second optical component assembly 16, having a fastening 26. The tension spring 25 has at the distal side end thereof a circumferential fastening ring 27, which engages in a guide groove 24 of the retainer 14" of the first optical component assembly 13. Thereby, the tension spring 25, using the fastening ring 27 thereof, can be rotated arbitrarily in the guide groove 24. The tension spring 25 pulls the retainer 17" in each case toward the retainer 14" in order to guarantee good optical quality at all times. The bearing in this case is a purely axial bearing 23.

Alternatively, the tension spring can also be fastened to the first optical component assembly and/or comprise a ball bearing for rotational bearing of the tubes, or respectively of the optical component assemblies.

FIG. 5 shows again an example of a radial axial bearing 20'', with which the retainer 17''' of the second optical component assembly 16 ends on the distal side in a circumferential guide rib 28, which in a similar manner to the example embodiment in FIG. 4, engages in a circumferential guide groove 24 of the retainer 14''' of the first optical component assembly 13. The guide rib 28 is produced from an elastic material, and is pretensioned in the engagement thereof in the guide groove 24. This means that in the position in which the retainer 17''' rests in the axial end position on the retainer 14''', the guide rib 28 is under an elastic tension, and exerts a further force in the direction of the distal end 11 of the shaft 2 on the retainer 17'''. The variant of FIG. 5 also shows an axial bearing according to the invention that is particularly simple and easy to construct.

All named characteristics, including those taken from the drawings alone, and individual characteristics, which are disclosed in combination with other characteristics, are considered individually and in combination as essential to the invention. Embodiments according to the invention can be fulfilled through individual characteristics or a combination of several characteristics.

REFERENCE LIST 1 endoscope
2 shaft
3 handle
4 rotary ring
5 bar magnet
6 outer tube
7 inner tube
8 radial bearing
9 compression spring
10 stop for compression spring
11 distal end
12 window
13 optical assembly with lenses and prisms
14, 14' retainer of the optical assembly
15 axial bearing
16 optical component assembly
17, 17' retainer of the optical assembly
18 radial bearing
19 image sensor unit
19a image sensor
20-20'' radial axial bearing
21 annular magnet
22 annular magnet
23 axial bearing
24 guide groove
25 tension spring
26 fastening
27 circumferential fastening ring
28 guide rib

What is claimed is:

1. An endoscope having a sideways viewing direction, comprising:
   a proximal handle,
   an endoscope shaft having an outer tube and an inner tube, and
   a first housing having a first optical component assembly mounted in an interior of the first housing, the first housing being mounted in a distal region of the endoscope shaft, the first housing having a proximal end formed by a first wall perpendicular to a longitudinal axis of the endoscope shaft and an external circumferential surface parallel to the longitudinal axis, the first optical component assembly being distally connected to the outer tube and comprises one or more of optical windows, prisms and lenses having a sideways viewing direction, a second housing having a second optical component assembly mounted in an interior of the second housing, the second housing being mounted proximally relative to the first housing, the second housing having a distal end having a second wall perpendicular to the longitudinal axis and an internal circumferential surface parallel to the longitudinal axis, the second optical component assembly being distally connected to the inner tube, the first wall and external circumferential surface of the first housing mating with the second wall and internal circumferential surface of the second housing to form an axial and radial bearing such that the first and second optical components assemblies can be rotated with respect to one another about the longitudinal axis of the endoscope shaft, a pretensioning device for biasing the second wall of the second housing in mating engagement with the first wall of the first housing; and an image sensor oriented relative to the second optical component assembly to receive incident light from the second optical component assembly;

wherein the pretensioning device is only disposed on one of the first and second housings; and at least one part of the axial and radial bearing and/or one of the first and second optical component assemblies have a ferromagnetic material, and the pretensioning device comprises a magnet by means of which the ferromagnetic material biases the second wall of the second housing in mating engagement with the first wall of the first housing.

2. The endoscope according to claim 1, wherein the magnet is an annular magnet.

3. The optical assembly according to claim 1, wherein the image sensor is oriented substantially perpendicular to the longitudinal axis of the endoscope shaft.

4. An optical assembly for an endoscope having a sideways viewing direction, the optical assembly comprising:

a first housing having a first optical component assembly mounted in an interior of the first housing, the first housing having a proximal end formed by a first wall perpendicular to a longitudinal axis of the first housing and an external circumferential surface parallel to the longitudinal axis, the first optical component assembly comprises one or more of optical windows, prisms and lenses having a sideways viewing direction, a second housing having a second optical component assembly mounted in an interior of the second housing, the second housing being mounted proximally relative to the first housing, the second housing having a distal end having a second wall perpendicular to the longitudinal axis and an internal circumferential surface parallel to the longitudinal axis, the first wall and external circumferential surface of the first housing mating with the second wall and internal circumferential surface of the second housing to form an axial and radial bearing such that the first and second optical components assemblies can be rotated with respect to one another about the longitudinal axis, a pretensioning device for biasing the second wall of the second housing in mating engagement with the first wall of the first housing; and an image sensor oriented relative to the second optical component assembly to receive incident light from the second optical component assembly;

wherein the pretensioning device is only disposed on one or more of the first and second housings; and at least one part of the axial and radial bearing and/or one of the first and second optical component assemblies have a ferromagnetic material, and the pretensioning device comprises a magnet by means of which the ferromagnetic material to bias the second wall of the second housing in mating engagement with the first wall of the first housing.

5. The optical assembly according to claim 4, wherein the magnet is an annular magnet.

6. The optical assembly according to claim 4, wherein the image sensor is oriented substantially perpendicular to the internal circumferential surface of the second housing.

* * * * *